United States Patent [19]

Gavish

[11] Patent Number: 5,423,328
[45] Date of Patent: Jun. 13, 1995

[54] STRESS DETECTING DEVICE AND METHOD FOR MONITORING BREATHING

[76] Inventor: Benjamin Gavish, P.O. Box 1141, Mevasseret Zion, Israel

[21] Appl. No.: 184,239

[22] Filed: Jan. 19, 1994

[30] Foreign Application Priority Data

Jan. 20, 1993 [IL] Israel ..................................... 104453

[51] Int. Cl.6 .............................................. A61B 5/08
[52] U.S. Cl. .................................... 128/721; 128/774
[58] Field of Search ............... 128/719, 721, 774, 782; 272/93, 125, DIG. 4–5

[56] References Cited

U.S. PATENT DOCUMENTS

| | | | |
|---|---|---|---|
| 3,402,222 | 1/1969 | Noe et al. | 128/782 |
| 4,296,757 | 10/1981 | Taylor | 128/782 X |
| 4,392,126 | 7/1983 | Loyola | 128/782 X |
| 4,595,196 | 6/1986 | Muchisky et al. | 128/721 X |
| 4,696,307 | 9/1987 | Montgieux | 128/721 |
| 4,846,462 | 7/1989 | Regnier et al. | 128/721 X |
| 5,064,192 | 11/1991 | Smith | 128/721 X |
| 5,107,846 | 4/1992 | Atlas | 128/721 X |
| 5,235,989 | 8/1993 | Zomer | 128/721 |
| 5,295,490 | 3/1994 | Dodakian | 128/721 |

Primary Examiner—Angela D. Sykes
Attorney, Agent, or Firm—Schneck & McHugh

[57] ABSTRACT

Stress detecting device for monitoring respiration, including a base supporting a transducer responsive to forces applied, at least indirectly, thereon by a slideably engageable belt, for producing electrical signals representative of magnitudes of the forces, and an element allowing at least one component of the forces in a selected direction to be applied to the transducer, while supressing application of other components in other directions of the forces to the transducer. A method for detecting and monitoring circumferential changes in the chest or abdomen of a user resulting from breathing, is also disclosed.

13 Claims, 2 Drawing Sheets

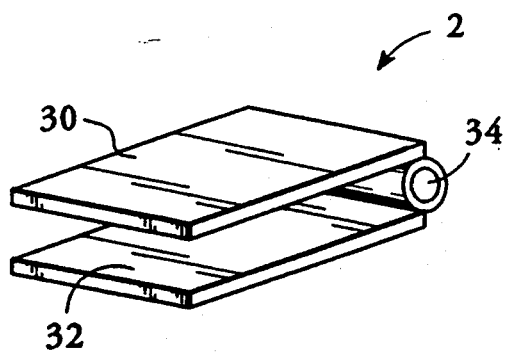
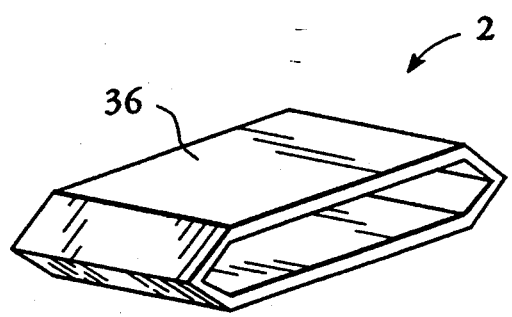
FIG. 5  FIG. 6
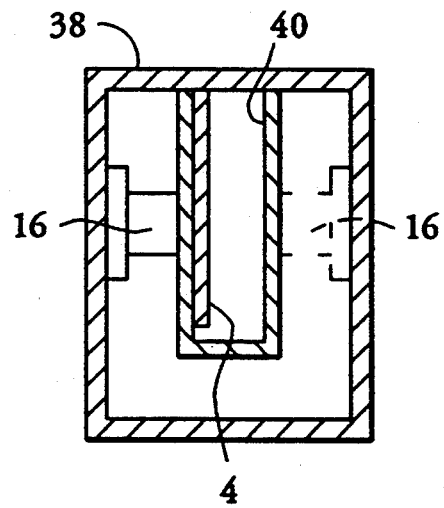
FIG. 7
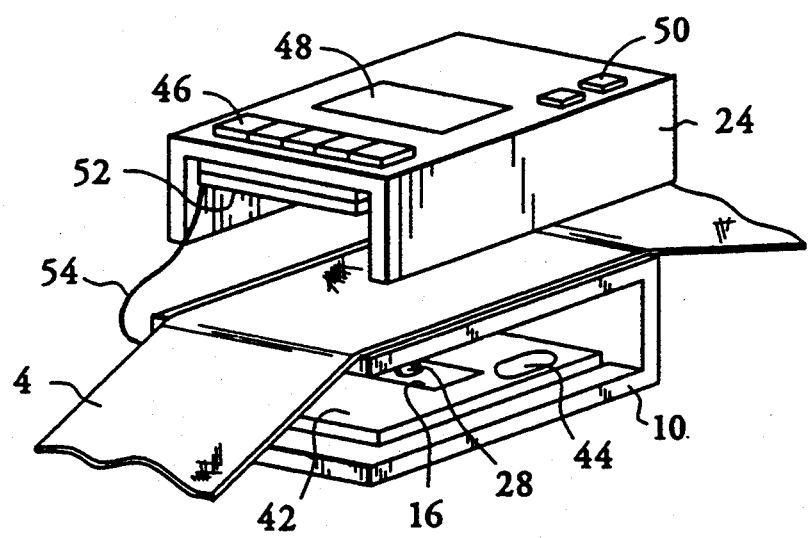
FIG. 8

STRESS DETECTING DEVICE AND METHOD FOR MONITORING BREATHING

BACKGROUND OF THE INVENTION

1. Field of the Invention

The present invention relates to a device and a method for monitoring breathing, and more particularly, to a stress detecting device for a sensor utilizable in the monitoring of breathing.

The invention is applicable for monitoring patients in hospitals; for monitoring vital signs under field conditions; as an additional channel to be utilized with portable volume ventilators; for monitoring apnea, as well as to be used in conjunction with health-care devices dedicated to breathing and relaxation exercises and for educational purposes, including interactive computer games that involve respiration functions.

2. Discussion of the Prior Art

Various devices are known and used for monitoring respiration by means of rhythmic variations in the circumference of the chest or abdomen that accompany the breathing movements of a user. For motionless users such as anesthesized patients, most types of respiration sensors work satisfactorily. There is, however, an increasing need for low-cost respiration monitors for awake and even moving users, for example:

a) Monitors utilized in conjunction with portable volume ventilators, to be used at home by patients suffering from chronic lung diseases requiring, for safety purposes, an independent channel for monitoring respiration;

b) Apnea monitors for home use;

c) Other types of healthcare products that involve a respiration monitor;

d) Computer-based educational products, which are based on multichannel monitoring of physiological variables, also including systems used for biofeedback processes, and e) Vital sign monitors to be used for mass casualties under field conditions, especially in case of, e.g., poisonous gases which were inhaled by patients that can cause severe breathing problems. This application requires the sensor used to minimize effects resulting from the movement of patients, which is unavoidable during transportation.

Most of the commercially available respiration sensors convert the rhythmic variations in the circumference of the chest or abdomen that accompany the breathing movements, into measureable electric signals. For example, known sensors measure variations of impedance between ECG electrodes attached to the chest, transient voltage or resistance changes generated, respectively, by piezoelectric or piezoresistive transducers, compressed or stretched by an elastic element, such as a belt or a sticky strip worn on the chest or abdomen, or by an elastic material on which the transducer is mounted.

The main problem with the known sensors is their great sensitivity to body movements not associated with respiration. This problem imposes serious limitations of the applications hereinbefore described. Hence, the problem of reducing the sensitivity of belt-type respiration sensors utilizing transducers to body movements of the measured signals requires the filtering out of undesired components, from the overall signals representing stresses applied by the belt to the transducer, in order to obtain a satisfactory sensor providing a reliable device for monitoring respiration.

SUMMARY OF THE INVENTION

In accordance with the present invention there is therefore provided stress detecting device for monitoring respiration, comprising a base supporting a transducer responsive to forces applied, at least indirectly, thereon by a slideably engageable belt, for producing electrical signals representative of magnitudes of said forces, and means allowing at least one component of said forces in a selected direction to be applied to said transducer, while supressing application of other components in other directions of said forces to the transducer.

The invention further provides stress detecting device, comprising a stretchable belt for converting deformations in the chest or abdomen of a user into mechanical stresses; a stress-filter base means slidably engaging said belt for selecting components of said mechanical stresses; a transducer converting said selected components into a measurable property; means for isolating said components produced by said transducer and cover means for protecting said stress-filter base means and transducer from forces other than those eminating from stretching of said belt when worn by, and as a result of circumferential changes in the chest or abdomen associated with breathing motions of, the user.

There is further provided a method for detecting and monitoring circumferential changes in the chest or abdomen of a user resulting from breathing, comprising surrounding said chest or abdomen with a stretchable belt, converting deformations of said chest or abdomen due to breathing into mechanical stresses in said belt, selecting from said mechanical stresses at least one component associated with variations in the length of said belt, and transducing said at least one component of mechanical stresses into electrical displayable biosignals.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

FIGS. 4 to 6 are perspective views of still further embodiments of devices according to the present invention;

FIG. 7 is a cross-sectional view of a double-sided detecting device according to the present invention, and FIG. 8 is a perspective view of a self-contained respiration detecting monitoring device according to the present invention.

DETAILED DISCUSSION OF THE PREFERRED EMBODIMENT

Figure 1:
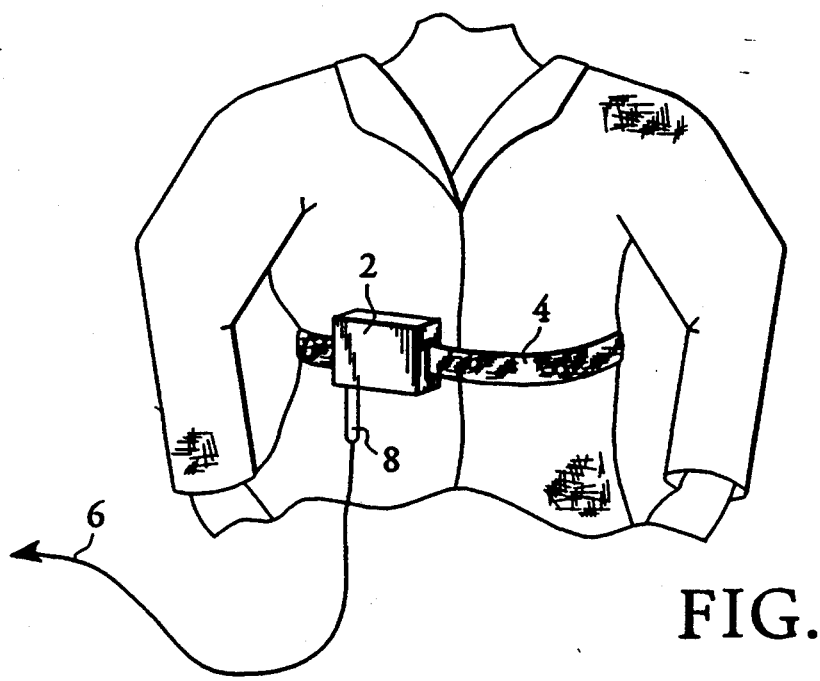
FIG. 1 is a perspective view of the slidable respiration sensor attached to a user's torso.

Referring to FIG. 1 there is seen a respiration sensor 2 slidably engaging an elastic or stretchable belt 4 worn on a user's clothing. The belt 4 may not necessarily be the kind stretchable along its entire length, but instead, it is sufficient that the belt include a stretchable portion only. The sensor's output signals can be transferred via an electrical or optical cable 6 to another device, transmitted by telemetrical means or displayed on the sensor 2 itself if it comprises a built-in visual monitor. The cable 6 may be protected from mechanical fatigue by a strain relief 8.

Figure 2:
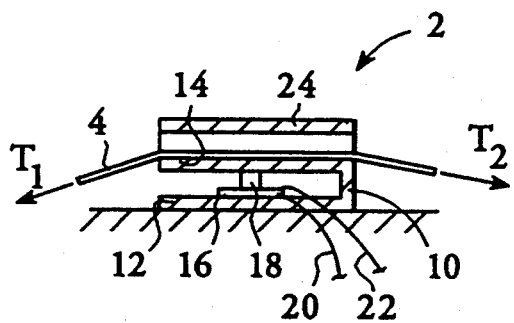
FIG. 2 is a cross-sectional view of a stress detecting device, according to the present invention.

Shown in FIG. 2, the sensor 2 comprises a base 10, having a U-shaped structure made of a material exhibiting some elasticity for angular deformation allowing changes in the angle between the legs 12 and 14 of the U-structure. Naturally, a V-shaped structure, having two interconnected diverging legs, could be utilized just as well. A force transducer 16 is fixedly attached e.g., by gluing to the inner surface of one leg of the base 10 and is mechanically linked via an elastic body member 18 to the other leg of the base 10. The output of the transducer 16, if electric, is supplied by two electrical wires 20,22. The sensor base 10 presses against the user's body by the stretchable belt 4. The displacement of the belt 4 in a direction perpendicularly to its length is limited by a cover 24 or by any other means, such as flanges, made on the base ! 0. The upper surface of the leg 14 is made to be smooth, and the cover 24 is configured so as not to touch the belt 4, and to allow the sensor to slide along the belt. By stretching the belt 4 around the user's chest or abdomen, the belt exerts forces on the base 10 which forces causes the base to stress. Since the U-shaped base 10 is able to be deformed only by forces applied in a direction substantially normal to one of the legs 12 or 14, the latter can transmit to the transducer 16 via the elastic member 18, a vectorial component in the same direction only, which component represents the resultant force stemming from the tensions T1 and T2 of the belt 4. For the same reason, torsional and shear stresses exerted by the belt 4 on the base 10 are eliminated or at least surpressed. The slidability of the sensor 2 along the belt 4 assures that if the resultant of the forces (tensions) T1 and T2 contains a non-zero longitudinal component, for example, along the belt, due to torsional chest movements, either the sensor 2 or the belt 4 (or both) will move with respect to each other to a new equilibrium location without generating a net longitudinal force on the transducer. Hence, the structure of base 10 and its mechanical coupling to the belt 4, establish a "stress filter" capable of isolating selected components from the belt tension, in a way that eliminates or at least minimizes, the effect of body motion not associated with said circumferential changes, in the output of the transducer.

Figure 3:
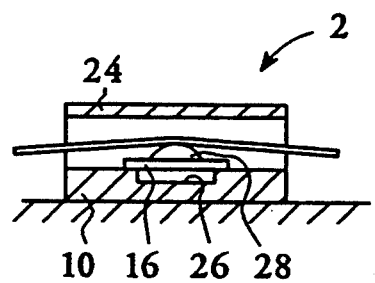
FIG. 3 is a cross-sectional view of a further embodiment of the device according to the present invention.

A second embodiment of the sensor 2 is illustrated in FIG. 3. According to this embodiment, the base 10 is planar and has a recess 26 made therein. The force transducer 16, preferably a piezo transducer, is affixed on the surface of the base across the recess 26. A smooth and rounded body member 28 is glued on, or otherwise attached to, the transducer 16. The cover 24 is similar to the one shown in FIG. 2. The curved top portion of the cap or cylindrical shape of the member 28 enables the belt 4 to slide thereon and thus constitutes, in conjunction with other parts of the device, a stress filter.

Figure 4:
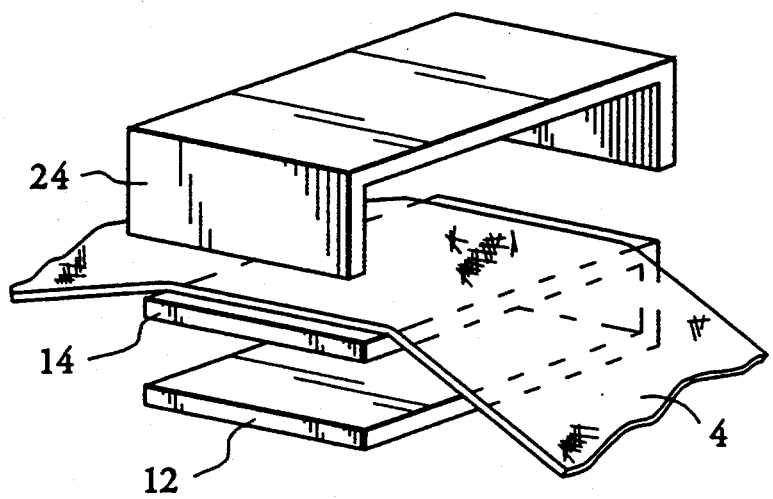

Another embodiment of the sensor 2 according to the present invention is depicted in FIG. 4. As seen in this embodiment, the direction of the legs 12 and 14 of the U-shaped base 10 is perpendicular to the axis of the belt 4, instead of parallel thereto as shown in FIG. 2. Also shown is a possible manner of engaging the cover 24 to the base 10, so as to isolate the base 10 and the transducer (not shown) from vertical forces acting on the cover 24.

Still other configurations for the sensor's base 10 are shown in FIGS. 5 and 6. In FIG. 5, base 10 is made of rigid plates 30,32 connected along one side thereof with a freely-rotating hinge 34. This structure provides great sensitivity to the stresses applied thereon by a belt without the creation of any restoring forces by itself. Instead, it transmits substantially all filtered stresses directly to the transducer/body member 16,28 combination. The base 10 of FIG. 6 is configured as a compressible flattened tube 36 and has the advantage of better protecting a transducer disposed therein. On each of these base structures the belt 4 could be placed in any orientation with respect thereto.

FIG. 7 shows an embodiment in which the base and the cover are integral or a single unit forming a rigid frame 38 housing an elastic box-like part 40, having two spaced-apart wall portions through which the belt 4 can pass. A transducer 16 is attached to an inner surface of the frame 38 and a body member 28 is disposed between the transducer and the elastic part 40. Similarly, a transducer/body member can also be disposed on the other side of the part 40 and an inner surface of the frame 38 (as shown by the hatched lines), so as to render the sensor symmetric with respect to its mountability on a belt and, in turn, onto a user and operation.

The bases 10 and/or covers 24 of most of the structures can be cut from extruded profiles, thereby considerably reducing manufacturing costs.

The operation of the respiration sensor and monitor according to the present invention will now become even more clear with the following description of FIG. 8 illustrating a self-contained slidable, respiration monitoring sensor. The transducer 16 is mechanically, as well as electrically, directly attached on a PC board 42 and the entire circuit is powered by a battery 44 also locates within the confines of the base. The electronic circuits for producing the desired biosignals by amplifying, filtering, processing and transmitting the output signals from the transducer 16, are per-se known and need not be described.

The cover 24 is used as a mount for the displays of the biosignals utilizing, for example, a light bar 46, and/or LCD 48, and controls 50 such as power on/off switches and selectors of modes of operation. The displayed information could be related to logical variables such as, inspiration/expiration and HI/LO alarms (audiovisual); analog signals indicating variations of lung volume (with DC type transducers); air flow (with AC type transducers); numeric information such as respiration period or rate; inspiration/expiration time ratios, etc. The electronic components of the display can be assembled on a second PC board 52 mounted below the cover 24, without touching the belt 4. PC boards 42 and 52 are electrically connected by a multiconductor cable 54. Such a monitor has the advantage of being compact and slidable, enabling its placement in a position comfortable for both the user, as well as the person watching the monitor.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. Stress detecting device for monitoring respiration, comprising:
   a base supporting a transducer responsive to forces applied, at least indirectly, thereon by a slideably engageable, at least partly elastic belt, said transducer producing electrical signals representative of magnitudes of said forces, and
   means allowing at least one component of said forces in a selected direction to be applied to said transducer, while suppressing application of other components in other directions of said forces to the transducer.

2. The device as claimed in claim 1, wherein said base is U or V-shaped having two interconnected legs and said transducer and means are located between said legs and affixed to an inner surface of at least one of said legs.

3. The device as claimed in claim 1, wherein said base is in the form of a plate and said transducer is affixed across a recess made therein.

4. The device as claimed in claim 1, wherein said base is constituted by two plates interconnected along one side thereof by a hinge allowing said plates to move with respect to each other in one degree of freedom only and said transducer is affixed in between said plates.

5. The device as claimed in claim 1, wherein said base is in the form of two plates hingedly interconnected along two opposite sides thereof and said transducer is affixed in between said plates.

6. The device as claimed in claim 1, wherein said base is in the form of a rigid tubular frame having inner surfaces and including two spaced-apart flexible wall portions and at least one transducer affixed between one of said surfaces and said wall portions.

7. The device as claimed in claim 1, wherein said base further comprises means, at least attachable thereto, for allowing movement of said belt with respect thereto in one direction only while delimiting movements of said belt in other directions.

8. The device as claimed in claim 7, wherein said means for allowing movement of said belt in one direction only are cover means having a U-shaped configuration sized to be inter-engaged and retained by said base.

9. The device as claimed in claim 1, further comprising self-powered electronic circuit and display means for processing and displaying signals as transduced by said transducer when forces are applied thereto.

10. The device as claimed in claim 1 further including an elastic body member connected to the transducer to transmit forces thereto, the member having a curved top edge to facilitate the sliding of the belt thereon.

11. The device as claimed in claim 1, wherein said belt is detachably engageable therewith in a manner allowing a relative reciprocal movement thereinbetween along the length of the belt.

12. Stress detecting device, comprising a stretchable belt for converting deformations in the chest or abdomen of a user into mechanical stresses; a stress-filter base means slidably engaging said belt for selecting components of said mechanical stresses; a transducer converting said selected components into a measurable property; means for isolating said components produced by said transducer and cover means for protecting said stress-filter base means and transducer from forces other than those eminating from stretching of said belt when worn by, and as a result of circumferential changes in the chest or abdomen associated with breathing motions of, the user.

13. A method for detecting and monitoring circumferential changes in the chest or abdomen of a user resulting from breathing, comprising:
   surrounding said chest or abdomen with a stretchable belt;
   converting deformations of said chest or abdomen due to breathing into mechanical stresses in said belt;
   detecting said mechanical stresses associated with chest or abdomen deformations due to breathing while reducing detection of stresses in said belt not associated with respiratory functions by having a base supporting a transducer slidably engaged with the stretchable belt; and
   transducing at least one component of said mechanical stresses into electrical displayable biosignals.

* * * * *